(12) United States Patent
McIntosh et al.

(10) Patent No.: US 9,717,775 B2
(45) Date of Patent: Aug. 1, 2017

(54) METHODS FOR TREATING PAIN AND SCREENING ANALGESIC COMPOUNDS

(75) Inventors: J. Michael McIntosh, Salt Lake City, UT (US); Baldomero M. Olivera, Salt Lake City, UT (US); Michael A. Ellison, Boulder, CO (US); Michelle Vincler, Winston-Salem, NC (US)

(73) Assignee: University of Utah Research Foundation, Salt Lake City, UT (US)

( * ) Notice: Subject to any disclaimer, the term of this patent is extended or adjusted under 35 U.S.C. 154(b) by 594 days.

(21) Appl. No.: 12/307,953

(22) PCT Filed: Jul. 17, 2007

(86) PCT No.: PCT/US2007/016163
§ 371 (c)(1),
(2), (4) Date: Apr. 24, 2009

(87) PCT Pub. No.: WO2008/011006
PCT Pub. Date: Jan. 24, 2008

(65) Prior Publication Data
US 2009/0203616 A1 Aug. 13, 2009

Related U.S. Application Data

(60) Provisional application No. 60/831,468, filed on Jul. 18, 2006.

(51) Int. Cl.
| | | |
|---|---|---|
| *A61K 38/03* | (2006.01) | |
| *A61K 38/10* | (2006.01) | |
| *C12Q 1/00* | (2006.01) | |
| *G01N 33/53* | (2006.01) | |
| *A61K 38/17* | (2006.01) | |
| *G01N 33/94* | (2006.01) | |

(52) U.S. Cl.
CPC ....... *A61K 38/1767* (2013.01); *G01N 33/944* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 6,958,323 B2 | 10/2005 | Olivera et al. | |
| 2003/0109670 A1* | 6/2003 | Olivera et al. ............... | 530/324 |
| 2005/0215480 A1 | 9/2005 | Livett et al. | |
| 2012/0220539 A1 | 8/2012 | McIntosh et al. | |

FOREIGN PATENT DOCUMENTS

| | | |
|---|---|---|
| EP | 1 090 991 A1 | 4/2001 |
| JP | 2002-534996 A | 10/2002 |
| JP | 2003-509045 A | 3/2003 |
| JP | 2005-500017 A | 1/2005 |
| JP | 2009-533355 A | 9/2009 |
| WO | WO97/35478 | * 10/1997 |
| WO | 00/44769 A1 | 8/2000 |
| WO | 00/44776 A1 | 8/2000 |
| WO | 02/064740 A2 | 8/2002 |
| WO | WO02/079236 | * 10/2002 |
| WO | WO2007/014432 | * 2/2007 |
| WO | WO2007/118270 | * 10/2007 |
| WO | WO2008011006 | 1/2008 |

OTHER PUBLICATIONS

Vincler et al (PNAS, 2006, vol. 103, pp. 17880-17884).*
Rothlin et al (Molecular Pharmacology, 2003, vol. 63, pp. 1067-1074).*
Durrenberger et al (BMC Neurology, 2006, pp. 1-11).*
Ballestero et al (Molecular Pharmacology, 2005, vol. 68, pp. 822-829).*
Elgoyhen et al (PNAS, 2001, vol. 98, pp. 3501-3506).*
Mensah-Brown et al (Cytokine, 2005, vol. 31, pp. 180-190).*
Johnson D.S. et al., "α-Conotoxin Imi Exhibits Subtype-Specific Nicotinic Acetylcholine Receptor Blockade: Preferential Inhibition of Homomeric α7 and α9 Receptors," Molecular Pharmocology, 48:194-199 (1995).
Khalil, Z. et al., "OPL152 ACV1, A Novel Alpha-Conotoxin, Promotes Functional Recovery in Injured Neurons and Reduces Oxidative Stress Levels," Journal of Neurological Sciences, Oral Platform Abstracts, vol. 238, pp. S84-S85, Nov. 10, 2005, Elsevier Scientific Publishing Co., Amsterdam, NL, XP027711165.
McIntosh, J.M. et al., "A Novel α-Conotoxin, PeIA, Cloned from Conus pergrandis, Discriminates Between Rat α9α10 and α7 Nicotinic Cholinergic Receptors," The Journal of Biological Chemistry, vol. 280, No. 34, Aug. 26, 2005, pp. 30107-30112, © 2005 The American Society for Biochemistry and Molecular Biology, Inc.
Ellison, M. et el., "α-RgIA: A Novel Conotoxin That Specifically and Potently Blocks the α9α10 nAChR," Biochemistry, vol. 45, No. 5, Feb. 1, 2006, pp. 1511-1517, © 2006 American Chemical Society.
Supplementary European Search Report, EP Application No. 07796903.8-2107 / 2051726 PCT/US2007016163, University of Utah Research Foundation, dated Jun. 11, 2012, 10 pages.
Japanese Office Action, JP Application No. 2009-520801, Drafting date: Jul. 18, 2012, 6 pages.
Satkunanathan, N. et al., "Alpha-conotoxin Vc1.1 Alleviates Neuropathic Pain and Accelerates Functional Recovery of Injured Neurones," Brain Research, 2005, vol. 1059, pp. 149-158.
Lustig, L. "Nicotinic Acetylcholine Receptor Structure and Function in the Efferent Auditory System," The Anatomical Record Part A, Mar. 20, 2006, pp. 424-434, copyright 2006 Wiley-Liss, Inc.
Japanese Office Action with English Translation, Patent Application No. JP 2009-520801, Drafting Date: Aug. 8, 2013, 9 pages.
Examination Report dated Feb. 24, 2012 in Australian Application No. 2007275764.
Examination Report dated Apr. 18, 2013 in Australian Application No. 2007275764.

(Continued)

*Primary Examiner* — Karen Canella
(74) *Attorney, Agent, or Firm* — Christensen O'Connore Johnson Kindness PLLC (57) ABSTRACT

The present invention relates to the use of compounds that block the α9α10 subtype of the nicotinic acetylcholine receptor (nAChR) for treating pain, such as neuropathic pain and inflammatory pain, and inflammatory disorders, such as arthritis. The present invention also relates to screening compounds to identify analgesic agents that block the α9α10 subtype of the nAChR.

12 Claims, 4 Drawing Sheets

(56) References Cited

OTHER PUBLICATIONS

Lee, et al., "Overexpression and Activation of the Alpha9-Nicotinic Receptor During Tumorigenesis in Human Breast Epithelial Cells", J. Natl Cancer Inst., 2010, vol. 102 (17), pp. 1322-1335.
Office Action dated Mar. 26, 2013 in Canadian Application No. 2,657,532.
Office Action mailed Mar. 5, 2015 in U.S. Appl. No. 13/289,494.
Office Action mailed Aug. 27, 2014 in U.S. Appl. No. 13/289,494.
Search Report & Written Opinion dated Apr. 9, 2008 in PCT Application No. PCT/US2007/016163.
Werle, et al., "Strategies to Improve Plasma Half Life Time of Peptide and Protein Drugs", Amino Acids, 2006, vol. 30, pp. 351-367.
Office Action dated Jun. 2, 2015 in Japanese Application No. 2014-116680.
Examination Report mailed Nov. 9, 2015, issued in corresponding Canadian Application No. 2,657,532, filed Jan. 12, 2009, 3 pages.

\* cited by examiner

| Residue | | IC$_{50}$ (nM) |
|---|---|---|
| Arginine |  | 3.2 |
| Citrulline |  | 2.4 |
| ω-nitro-arginine |  | 2.3 |
| Homo-arginine |  | >1000 |
| Ornithine |  | >1000 |
| δ-N-acetyl-ornithine |  | >1000 |
| Lysine |  | >1000 |

Figure 6

SEQUENCE LISTING

```
<160> NUMBER OF SEQ ID NOS: 4

<210> SEQ ID NO 1
<211> LENGTH: 13
<212> TYPE: PRT
<213> ORGANISM: Conus regius

<400> SEQUENCE: 1

Gly Cys Cys Ser Asp Pro Arg Cys Arg Tyr Arg Cys Arg
1               5                   10

<210> SEQ ID NO 2
<211> LENGTH: 16
<212> TYPE: PRT
<213> ORGANISM: Conus victoriae

<400> SEQUENCE: 2

Gly Cys Cys Ser Asp Pro Arg Cys Asn Tyr Asp His Pro Glu Ile Cys
1               5                   10                  15

<210> SEQ ID NO 3
<211> LENGTH: 16
<212> TYPE: PRT
<213> ORGANISM: Conus pergrandis

<400> SEQUENCE: 3

Gly Cys Cys Ser His Pro Ala Cys Ser Val Asn His Pro Glu Leu Cys
1               5                   10                  15

<210> SEQ ID NO 4
<211> LENGTH: 20
<212> TYPE: PRT
<213> ORGANISM: Conus arenatus

<400> SEQUENCE: 4

Asp Glu Cys Cys Ser Asn Pro Ala Cys Arg Leu Asn Asn Pro His Ala
1               5                   10                  15

Cys Arg Arg Arg
            20
```

METHODS FOR TREATING PAIN AND SCREENING ANALGESIC COMPOUNDS

CROSS-REFERENCE TO RELATED APPLICATION

The present application is a national stage filing under 35 U.S.C. §371 of PCT/US2007/016163, filed on 17 Jul. 2007 which in turn claims priority under 35 U.S.C. §119(e) to U.S. provisional patent application Ser. No. 60/831,468 filed on 18 Jul. 2006, incorporated herein by reference.

REFERENCE TO GOVERNMENT SUPPORT

This invention was made with Government support under Grant Nos. MH 53631, GM48677 and NS048158 awarded by the National Institutes of Health, Bethesda, Md. The United States Government has certain rights in the invention.

BACKGROUND OF THE INVENTION

The present invention relates to the use of compounds that block the α9α10 subtype of the nicotinic acetylcholine receptor (nAChR) for treating pain, such as neuropathic pain and inflammatory pain, and inflammatory disorders, such as rheumatic diseases. The present invention also relates to screening compounds to identify analgesic agents that block the α9α10 subtype of the nAChR.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Predatory marine snails in the genus *Conus* have venoms that are rich in neuropharmacologically active peptides (Armishaw and Alewood, 2005; Wang and Chi, 2004; Livett et al., 2004; Lewis, 2004; Terlau and Olivera, 2004). There are approximately 500 species in *Conus*, and among those that have been examined so far, a conserved feature is the presence of α-conotoxins in their venom. These are highly disulfide cross-linked peptides with the disulfide scaffold of C1-C3 and C2-C4. Due to high sequence variability of their non-cysteine residues α-conotoxins are extremely diverse and each *Conus* species has a unique complement of α-conotoxins. α-Conotoxins are synthesized as large precursors, and the mature toxin is generated by a proteolytic cleavage toward the C-terminus of the precursor. In contrast to the variable inter-cysteine sequences of the mature toxins, the precursors and the genes encoding them are quite conserved both among α-conotoxins in a given *Conus* species and from species to species. α-Conotoxins have generally been shown to be nicotinic acetylcholine receptor (nAChR) antagonists (McIntosh et al., 1999; Janes, 2005; Dutton and Craik, 2001; Arias and Blanton, 2000).

nAChRs are a group of acetylcholine gated ion channels that are part of the ligand gated ion channel superfamily (Karlin, 2002; Gotti and Clementi, 2004). They are pentamers of transmembrane subunits surrounding a central ion conducting channel. Many different subunits have been identified, and most fall into two main subfamilies (the α subunits and the β subunits). The subunits can associate in various combinations in the receptor pentamers, leading to a diverse family of receptor subtypes. Most of the subtypes contain subunits from both the α and β subunit families, e.g., the human adult muscle subtype contains two α1 subunits and a β1 subunit (in addition to a δ and an ε subunit) and the α3β2 subtype is composed of α3 and β2 subunits. nAChRs that are composed of only α subunits are the α7 and α9 subtypes (homopentamers) and the α9α10 subtype (an all α heteropentamer). Phylogenetic analysis shows that the α7, α9, and α10 subunits are more closely related to each other than they are to other nAChR subunits (Le Novere et al., 2002; Sgard et al., 2002).

The α9 and α10 nAChR subunits are expressed in diverse tissues. In the inner ear α9α10 nAChRs mediate synaptic transmission between efferent olivocochlear fibers and cochlear hair cells (Sgard et al., 2002; Elgoyhen et al., 1994; Elgoyhen et al., 2001). The α9 and α10 subunits are also found in dorsal root ganglion neurons (Harberger et al., 2004; Lips et al., 2002), lymphocytes (Peng et al., 2004), skin keratinocytes (Arredondo et al., 2002; Nguyen et al., 2000; Kurzen et al., 2004), and the pars tuberalis of the pituitary (Sgard et al., 2002; Elgoyhen et al., 1994; Elgoyhen et al., 2001).

There are drugs used in the treatment of pain, which are known in the literature and to the skilled artisan. See, for example, *The Merck Manual of Diagnosis and Therapy*, 17th Edition (1999). However, there is a demand for more active analgesic agents with diminished side effects and toxicity and which are non-addictive. The ideal analgesic would reduce the awareness of pain, produce analgesia over a wide range of pain types, act satisfactorily whether given orally or parenterally, produce minimal or no side effects, be free from tendency to produce tolerance and drug dependence.

SUMMARY OF THE INVENTION

The present invention relates to the use of compounds that block the α9α10 subtype of the nicotinic acetylcholine receptor (nAChR) for treating pain, such as neuropathic pain and inflammatory pain, and inflammatory disorders, such as rheumatic diseases. The present invention also relates to screening compounds to identify analgesic agents that block the α9α10 subtype of the nAChR.

Thus, in one aspect, the present invention demonstrates that certain α-conotoxins block the α9α10 subtype of the nAChR. Such α-conotoxins include, but are not limited to, α-conotoxin RgIA (GCCSDPRCRYRCR; SEQ ID NO:1), α-conotoxin Vc1.1 (GCCSDPRCNYD HPEIC; SEQ ID NO:2) and α-conotoxin PeIA (GCCSHPACSVNHPELC; SEQ ID NO:3).

In a second aspect, the present invention demonstrates that certain analogs or derivatives of α-conotoxins RgIA, Vc1.1, PeIA and ArIB [V11L;V16A] (DECCSNPACRLN-NPHACRRR; SEQ ID NO:4) also block the α9α10 subtype of the nAChR. Such analogs include RgIA analogs in which (i) $Arg_9$ is substituted with citrulline or ω-nitro-Arg, (ii) $Tyr_{10}$ is substituted with iodo-Tyr, Trp or Phe, (iii) $Ser_4$ is substituted with Ala, (iv) deltaArg$_{13}$,Cys$_{12}$-amide, (v) additions are made to the C-terminus, such as Tyr, iodo-Tyr, a fluorescent tag, (vi) additions are made to the N-terminus, such as Tyr, iodo-Tyr, pyroglutamate or a fluorescent tag or (vii) any combination of these. Other analogs include Vc1.1 analogs in which (i) $Glu_{14}$ is substituted with iodo-His, iodo-Tyr, iodo-Phe or iodo-Trp, (ii) additions are made to the C-terminus, such as Tyr, iodo-Tyr, fluorescent tag, (iii) additions are made to the N-terminus, such as Tyr, iodo-Tyr, pyroglutamate or a fluorescent tag or (iv) any combination of these. Additional analogs include PeIA analogs in which (i) $Glu_{14}$ is substituted with iodo-His, iodo-Tyr, iodo-Phe or iodo-Trp, (ii) additions are made to the C-terminus, such as Tyr, iodo-Tyr, fluorescent tag, (iii) additions are made to the N-terminus, such as Tyr, iodo-Tyr, pyroglutamate or a fluorescent tag or (iv) any combination of these. Other analogs include ArIB [V11L;V16A] in which (i) $His_{15}$ is substituted with iodo-His, iodo-Tyr, iodo-Phe or iodo-Trp, (ii) additions are made to the C-terminus of (i), such as Tyr, iodo-Tyr, fluorescent tag, (iii) additions are made to the N-terminus of (i), such as Tyr, iodo-Tyr, pyroglutamate or a fluorescent tag or (iv) any combination of these. In addition, residues or groups of residues known to the skilled artisan to improve stability can be added to the C-terminus and/or N-terminus. Also, residues or groups of residues known to the skilled artisan to improve oral availability can be added to the C-terminus and/or N-terminus. In addition, the above residues or groups that can be added to the C-terminus can also replace $Arg_{13}$ in RgIA. Finally, the above residues or groups that can be added to the N-terminus can also replace the $Gly_1$ in RgIA, Vc1.1 and PeIA.

In a third aspect, the present invention demonstrates that the α9α10 subtype of the nAChR is involved with pain, and the blockage of this receptor is useful in treating pain, including chronic pain, neuropathic pain and inflammatory pain, and other inflammatory conditions or disorders.

In a fourth aspect, the present invention demonstrates that the α9α10 subtype of the nAChR is involved with the migration of immune cells and the blockage of this receptor is useful for inhibiting the migration of immune cells, for treating inflammatory conditions or disorders and for reducing inflammation such as associated with rheumatic diseases.

In a fifth aspect, the present invention provides methods for identifying compounds that block the α9α10 subtype of the nAChR. Such compounds are drug candidates for use as analgesics, for use in inhibiting the migration of immune cells, for use in treating inflammatory conditions or disorders and for use in reducing inflammation.

BRIEF DESCRIPTION OF THE FIGURES

FIGS. 1A and 1B show the activity of α-CTx on nAChRs. α-CTxs were bath applied to oocytes expressing the indicated nAChR subtypes and then the response to a 1 s pulse of ACh was measured as described in Example 1. FIG. 1A: α-Ctx RgIa blocks α9α10 and α1β1δε nAChRs with an $IC_{50}$s of 4.8 (4.0-5.8) nM and 16.1 mM and Hill slopes of 1.13±0.11 and 0.931±0.40 respectively. FIG. 1B: α-Ctx Vc1.1 blocks α9α10, α6/α3β2β3 and α6/α3β4 nAChRs with $IC_{50}$s of 22.9 (13.6-38.4) nM and 144 (90.9-229) and 982 (751-1,283) nM respectively and Hill slopes of 0.702±0.11, 1.21±0.27 and 1.28±0.1.6 respectively. See Table 1 for comparison to activity at other nAChR subtypes. ( )=95% confidence interval; ± is the standard error of the mean.

DETAILED DESCRIPTION OF THE FIGURES

The present invention relates to the use of compounds that block the α9α10 subtype of the nicotinic acetylcholine receptor (nAChR) for treating pain, including neuropathic pain and inflammatory pain, for inhibiting migration of immune cells, for treating inflammatory disorders and for reducing inflammation associated with disorders such as rheumatic diseases. The present invention also relates to screening compounds to identify agents that block the α9α10 subtype of the nAChR. Such agents are useful in the same manner as the α-conotoxins described herein.

The activity of the α-conotoxins in blocking the α9α10 subtype of the nAChR is shown herein in studies using oocytes that express different subtypes of the nAChR. The activity of α-conotoxins in inhibiting migration of immune cells is shown herein in studies of chronic constriction injury. α-conotoxins that have been shown to have these activities are α-conotoxin RgIA and α-conotoxin Vc1.1. In addition, α-conotoxin PeIA has been shown to be selective for the α9α10 subtype of the nAChR (McIntosh et al., 2005). Compounds that block the α9α10 nAChR are useful as analgesic agents, as agents for inhibiting the migration of immune cells, as agents for treating inflammatory pain and other inflammatory conditions or disorders and as agents for reducing inflammation associated with disorders such as rheumatic diseases. Inflammatory conditions include, but are not limited to, sepsis, fibromyalgia, inflammatory bowel disease (including; but not limited to ulcerative colitis and Crohn's disease), sarcoidosis, endometriosis, uterine fibroids, inflammatory skin diseases including but not limited to psoriasis, impaired wound healing, inflammatory conditions of the lungs including, but not limited to asthma and chronic obstructive pulmonary disease, diseases associated with inflammation of the nervous system including Parkinson's Disease and Alzheimer's Disease, periodontal disease, and cardiovascular disease. Rheumatic diseases include, but are not limited to, arthritis, lupus, ankylosing spondylitis, fibromyalgia, tendonitis, bursitis, scleroderma, and gout.

Thus, the present invention relates to a method for treating or preventing conditions or disorders associated with the α9α10 subtype of the nicotinic acetylcholine receptor (nAChR) in an individual which comprises administering to an individual in need thereof a therapeutically effective amount of an active agent or a pharmaceutically acceptable salt thereof, wherein the active agent blocks the α9α10 subtype of the nAChR. In one embodiment, the condition is pain and the administration of the active agent alleviates pain in the individual. In a second embodiment, the condition is inflammation mediated by immune cells and the administration of the active agent reduces inflammation. In one embodiment, the inflammation is associated with rheumatic diseases.

The present invention also relates to a method of inhibiting migration of immune cells in an individual in need thereof which comprises administering to an individual an immune cell migration-inhibiting amount of an active agent or a pharmaceutically acceptable salt thereof, wherein said active agent blocks the α9α10 subtype of the nicotinic acetylcholine receptor (nAChR).

The present invention further relates to a method for identifying drug candidates for use as treating or preventing conditions or disorders associated with the α9α10 subtype of the nicotinic acetylcholine receptor (nAChR) or for inhibiting the migration immune cells which comprises screening a drug candidate for its ability to block the activity of the α9α10 subtype of the nAChR. In one embodiment, the displacement of a labeled α-conotoxin from the α9α10 subtype of the nAChR by a candidate drug agent is used to identify suitable candidate drugs. In a second embodiment, a biological assay on a drug candidate to determine the therapeutic activity is conducted and compared to the results obtained from the biological assay of the α-conotoxin. In a third embodiment, the binding affinity of a drug candidate to the α9α10 subtype of the nAChR is measured and compared to the binding affinity of a α-conotoxin to the α9α10 subtype of the nAChR. In a fourth embodiment, the effect of a drug candidate on the function of the α9α10 subtype of the nAChR is analyzed by measuring the effect in functional assays, such as electrophysiological assays, calcium imaging assays and the like. These latter assays can measure the ability of the drug candidate to block the function of α9 homomers and/or α9α10 heteromers.

The present invention also relates to a method of identifying compounds that mimic the therapeutic activity of an α-conotoxin, comprising the steps of: (a) conducting a biological assay on a test compound to determine the therapeutic activity; and (b) comparing the results obtained from the biological assay of the test compound to the results obtained from the biological assay of the α-conotoxin.

Thus, the present invention also relates to rational drug design for the identification of additional drugs which can be used for the purposes described herein. The goal of rational drug design is to produce structural analogs of biologically active polypeptides of interest or of small molecules that also act on the receptor (e.g., agonists, antagonists, inhibitors) in order to fashion drugs which are, for example, more active or stable forms of the polypeptide, or which, e.g., enhance or interfere with the function of a polypeptide in vivo. Several approaches for use in rational drug design include analysis of three-dimensional structure, alanine scans, molecular modeling and use of anti-id antibodies. These techniques are well known to those skilled in the art. Such techniques may include providing atomic coordinates defining a three-dimensional structure of a protein complex formed by said first polypeptide and said second polypeptide, and designing or selecting compounds capable of interfering with the interaction between a first polypeptide and a second polypeptide based on said atomic coordinates.

Following identification of a substance which modulates or affects polypeptide activity, the substance may be further investigated. Furthermore, it may be manufactured and/or used in preparation, i.e., manufacture or formulation, or a composition such as a medicament, pharmaceutical composition or drug. These may be administered to individuals.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This approach might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

A template molecule is then selected, onto which chemical groups that mimic the pharmacophore can be grafted. The template molecule and the chemical groups grafted thereon can be conveniently selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent it is exhibited. Further optimization or modification can then be carried out to arrive at one or more final mimetics for in vivo or clinical testing.

The present invention further relates to the use of a labeled (e.g., radiolabel, fluorophore, chromophore or the like) of the conotoxins described herein as a molecular tool both in vitro and in vivo, for discovery of small molecules that exert their action at or partially at the same functional site as the native toxin and capable of elucidation similar functional responses as the native toxin. In one embodiment, the displacement of a labeled conotoxin from its receptor, i.e., α9α10 nAChR, or other complex by a candidate drug agent is used to identify suitable candidate drugs. In a second embodiment, a biological assay on a test compound to determine the therapeutic activity is conducted and compared to the results obtained from the biological assay of a conotoxin. In a third embodiment, the binding affinity of a small molecule to the receptor of a conotoxin, i.e., α9α10 nAChR, is measured and compared to the binding affinity of a conotoxin to its receptor, i.e., α9α10 nAChR. In a fourth embodiment, the effect of a drug candidate on the function of the α9α10 subtype of the nAChR is analyzed by measuring the effect in functional assays, such as electrophysiological assays, calcium imaging assays and the like. In this manner, candidate drugs are identified that block the α9α10 nAChR and are useful as analgesic agents, as agents for inhibiting the migration of immune cells, as agents for treating inflammatory pain and other inflammatory disorders and as agents for reducing inflammation, such as inflammation associated with arthritis.

Pharmaceutical compositions containing a compound of the present invention as the active ingredient can be prepared according to conventional pharmaceutical compounding techniques. See, for example, *Remington: The Science*

*and Practice of Pharmacy,* 21st Ed., Lippincott Williams & Wilkins, Philadelphia, 2005. Typically, an antagonistic amount of active ingredient will be admixed with a pharmaceutically acceptable carrier. The carrier may take a wide variety of forms depending on the form of preparation desired for administration, e.g., intravenous, oral, parenteral or intrathecally. For examples of delivery methods see U.S. Pat. No. 5,844,077, incorporated herein by reference.

"Pharmaceutical composition" means physically discrete coherent portions suitable for medical administration. "Pharmaceutical composition in dosage unit form" means physically discrete coherent units suitable for medical administration, each containing a daily dose or a multiple (up to four times) or a sub-multiple (down to a fortieth) of a daily dose of the active compound in association with a carrier and/or enclosed within an envelope. Whether the composition contains a daily dose, or for example, a half, a third or a quarter of a daily dose, will depend on whether the pharmaceutical composition is to be administered once or, for example, twice, three times or four times a day, respectively.

The term "salt", as used herein, denotes acidic and/or basic salts, formed with inorganic or organic acids and/or bases, preferably basic salts. While pharmaceutically acceptable salts are preferred, particularly when employing the compounds of the invention as medicaments, other salts find utility, for example, in processing these compounds, or where non-medicament-type uses are contemplated. Salts of these compounds may be prepared by art-recognized techniques.

Examples of such pharmaceutically acceptable salts include, but are not limited to, inorganic and organic addition salts, such as hydrochloride, sulphates, nitrates or phosphates and acetates, trifluoroacetates, propionates, succinates, benzoates, citrates, tartrates, fumarates, maleates, methane-sulfonates, isothionates, theophylline acetates, salicylates, respectively, or the like. Lower alkyl quaternary ammonium salts and the like are suitable, as well.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, aloha-tocopherol and the like; and the metal chelating agents such as citric acid, ethylenediamine tetraacetic acid (EDTA), sorbitol, tartaric acid, phosphoric acid and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, epidural, irrigation, intramuscular, release pumps, or infusion.

For example, administration of the active agent according to this invention may be achieved using any suitable delivery means, including:

(a) pump (see, e.g., Luer and Hatton (1993), Zimm et al. (1984) and Ettinger et al. (1978));

(b), microencapsulation (see, e.g., U.S. Pat. Nos. 4,352,883; 4,353,888; and 5,084,350);

(c) continuous release polymer implants (see, e.g., U.S. Pat. No. 4,883,666);

(d) macroencapsulation (see, e.g., U.S. Pat. Nos. 5,284,761, 5,158,881, 4,976,859 and 4,968,733 and published PCT patent applications WO92/19195, WO 95/05452);

(e) naked or unencapsulated cell grafts to the CNS (see, e.g., U.S. Pat. Nos. 5,082,670 and 5,618,531);

(f) injection, either subcutaneously, intravenously, intra-arterially, intramuscularly, or to other suitable site; or (g) oral administration, in capsule, liquid, tablet, pill, or prolonged release formulation.

In one embodiment of this invention, an active agent is delivered directly into the CNS, preferably to the brain ventricles, brain parenchyma, the intrathecal space or other suitable CNS location, most preferably intrathecally.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Active agents, which may be peptides, can also be administered in a cell based delivery system in which a DNA sequence encoding an active agent is introduced into cells designed for implantation in the body of the patient, especially in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959 and WO 97/12635. Suitable DNA sequences can be prepared synthetically for each active agent on the basis of the developed sequences and the known genetic code.

The active agent is preferably administered in a therapeutically effective amount. By a "therapeutically effective amount" or simply "effective amount" of an active compound is meant a sufficient amount of the compound to treat the desired condition at a reasonable benefit/risk ratio applicable to any medical treatment. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in Remington: The Science and Practice of Pharmacy.

Dosage may be adjusted appropriately to achieve desired drug levels, locally or systemically. Typically the active agents of the present invention exhibit their effect at a dosage range from about 0.001 mg/kg to about 250 mg/kg, preferably from about 0.01 mg/kg to about 100 mg/kg of the active ingredient, more preferably from a bout 0.05 mg/kg to about 75 mg/kg. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form. Dosages are generally initiated at lower levels and increased until desired effects are achieved. In the event that the response in a subject is insufficient at such doses, even higher doses (or effective higher doses by a different, more localized delivery route) may be employed to the extent that patient tolerance permits. Continuous dosing over, for example, 24 hours or multiple doses per day are contemplated to achieve appropriate systemic levels of compounds.

Advantageously, the compositions are formulated as dosage units, each unit being adapted to supply a fixed dose of active ingredients. Tablets, coated tablets, capsules, ampoules and suppositories are examples of dosage forms according to the invention.

It is only necessary that the active ingredient constitute an effective amount, i.e., such that a suitable effective dosage will be consistent with the dosage form employed in single or multiple unit doses. The exact individual dosages, as well as daily dosages, are determined according to standard medical principles under the direction of a physician or veterinarian for use humans or animals.

The pharmaceutical compositions will generally contain from about 0.0001 to 99 wt. %, preferably about 0.001 to 50 wt. %, more preferably about 0.01 to 10 wt. % of the active ingredient by weight of the total composition. In addition to the active agent, the pharmaceutical compositions and medicaments can also contain other pharmaceutically active compounds. Examples of other pharmaceutically active compounds include, but are not limited to, analgesic agents, cytokines and therapeutic agents in all of the major areas of clinical medicine. When used with other pharmaceutically active compounds, the active agents of the present invention may be delivered in the form of drug cocktails. A cocktail is a mixture of any one of the compounds useful with this invention with another drug or agent. In this embodiment, a common administration vehicle (e.g., pill, tablet, implant, pump, injectable solution, etc.) would contain both the instant composition in combination with a supplementary potentiating agent. The individual drugs of the cocktail are each administered in therapeutically effective amounts. A therapeutically effective amount will be determined by the parameters described above; but, in any event, is that amount which establishes a level of the drugs in the area of body where the drugs are required for a period of time which is effective in attaining the desired effects.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., *Molecular Cloning* (Cold Spring Harbor Laboratory Press, Cold Spring Harbor, N.Y., 1982); Sambrook et al., *Molecular Cloning*, 2nd Ed. (Cold Spring Harbor Laboratory Press, Cold Spring Harbor, N.Y., 1989); Sambrook and Russell, *Molecular Cloning*, 3rd Ed. (Cold Spring Harbor Laboratory Press, Cold Spring Harbor, N.Y., 2001); Ausubel et al., *Current Protocols in Molecular Biology* (John Wiley & Sons, updated through 2005); Glover, *DNA Cloning* (IRL Press, Oxford, 1985); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, *Antibodies*, (Cold Spring Harbor Laboratory Press, Cold Spring Harbor, N.Y., 1998); Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, A *Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, (Blackwell Scientific Publications, Oxford, 1988); Hogan et al., *Manipulating the Mouse Embryo*, (Cold Spring Harbor Laboratory Press, Cold Spring Harbor, N.Y., 1986); Westerfield, M., *The zebrafish book. A guide for the*

*laboratory use of zebra fish (Danio rerio)*, 4th Ed., (Univ. of Oregon Press, Eugene, Oreg., 2000).

EXAMPLES

The present invention can be described by reference to the following Examples, which are offered by way of illustration and are not intended to limit the invention in any manner. Standard techniques well known in the art or the techniques specifically described below were utilized.

Example 1 nAChR Studies

Methods

The oocyte recording chamber was fabricated from Sylgard and was 30 µl in volume. Oocytes were gravity-perfused with ND96 (96.0 mM NaCl, 2.0 mM KCl, 1.8 mM $CaCl_2$, 1.0 mM $MgCl_2$, 5 mM HEPES, pH 7.1-7.5) containing 1 µM atropine (ND96A) with or without toxin at a rate of ~1 ml/min. All solutions also contained 0.1 mg/ml bovine serum albumin (BSA) to reduce nonspecific adsorption of peptide. The perfusion medium could be switched to one containing peptide or ACh by use of a series of three-way solenoid valves (model 161T031, Neptune Research, Northboro, Mass.). All recordings were made at room temperature (~22° C.). Oocytes were harvested and injected with cRNA encoding rat neuronal and human muscle nAChR subunits as described previously (Azam et al., 2005; Ellison et al., 2006) with the α6α3 chimera Ala278 corrected to Val. ACh-gated currents were obtained with a two-electrode voltage-clamp amplifier (model OC-725B, Warner Instrument, Hamden, Conn.). The membrane potential was clamped at −70 mV, and the current signal, recorded through virtual ground, was low-pass-filtered (5 Hz cut-off) and digitized at a sampling frequency of 20 Hz.

To apply a pulse of ACh to the oocyte, the perfusion fluid was switched to one containing ACh for 1 sec. This was automatically done at intervals of 1-2 min. The shortest time interval was chosen such that reproducible control responses were obtained with no observable desensitization. This time interval depended on the nAChR subtype being tested. The concentration of ACh was 200 µM for α7, 10 µM for α1β1ε and α9α10 and 100 µM for all other subtypes. The ACh was diluted in ND96A for tests of all nAChR subtypes except α7 and α9α10 in which case the diluent was ND96. For control responses, the ACh pulse was preceded by perfusion with ND96 (for α7 and α9α10) or ND96A (all others). No atropine was used with oocytes expressing α7 and α9α10, because it has been demonstrated to be an antagonist of α7-like receptors (Gerzanich et al., 1994). For test responses, toxin was bath applied for 5 minutes prior to subsequent exposure to ACh. All ACh pulses contained no toxin, for it was assumed that little, if any, bound toxin would have washed away in the brief time (<2 sec) it takes for the responses to peak. The average peak amplitude of three control responses just preceding exposure to toxin were used to normalize the amplitude of each test response to obtain "% response" or "% block."

Results

Figure 1A:
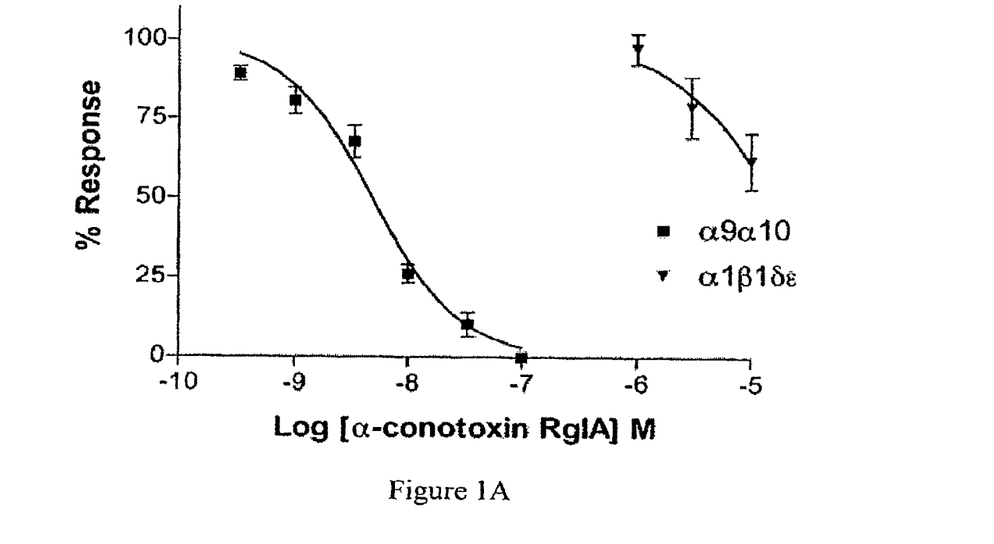
Figure 1B:
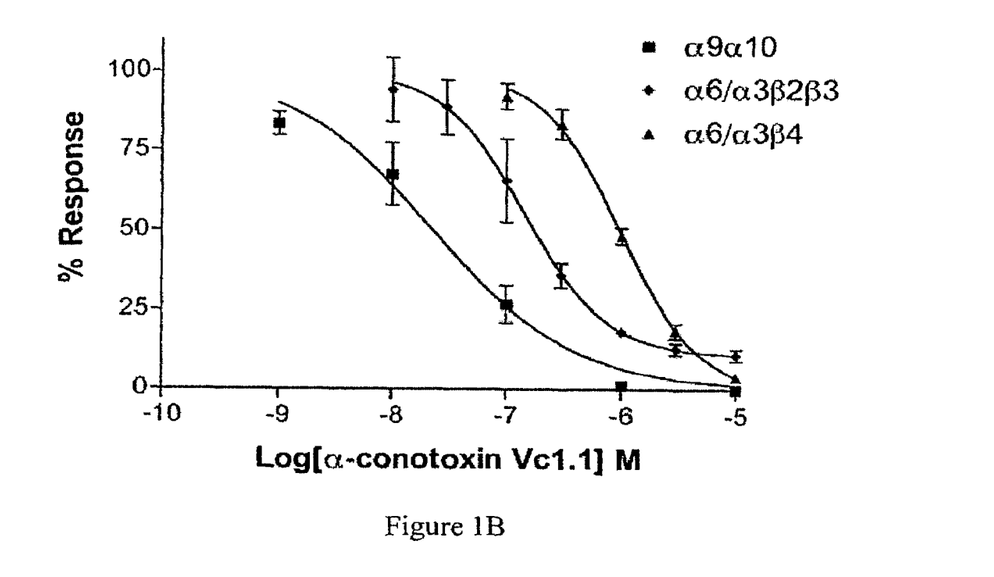

*Xenopus* oocytes were used to heterologously express cloned nAChR subtypes. α-Ctx RgIA potently blocks the ACh-induced current in α9α10 vs. muscle nAChR subtypes as shown in FIG. 1. The potent analgesic activity of α-Ctx RgIA in the SCI model resembles that seen with an analgesic conotoxin known as α-Ctx Vc1.1. This peptide, also known as ACV1 is undergoing human clinical trials for the treatment of neuropathic pain; however, its receptor subtype mechanism of action has remained elusive (Sandall et al., 2003; Lang et al., 2005; Satkunanathan et al., 2005; Clark et al., 2006). As shown in FIG. 1, α-Ctx Vc1.1 also potently blocks the α9α10 subtype of nAChR. Whereas α-Ctx RgIA is highly selective for the α9α10 nAChR, α-Ctx Vc1.1 also has comparatively significant activity at α6-containing nAChRs (Table 1).

TABLE 1

Selectivity of Analgesic α-Conotoxins

| nAChR subtype | *RgIA $IC_{50}$ | *Vc1.1 $IC_{50}$ |
|---|---|---|
| α9α10 | 4.8[1] | 22.9[1] |
| α1β1ε | 16,200[1] | ND |
| α1β1γ | ND | >30,000[3] |
| α2β2 | >10,000[2] | >10,000[3] |
| α2β4 | >10,000[2] | >10,000[3] |
| α3β2 | >10,000[2] | 7,300[3] |
| α3β4 | >10,000[2] | 4,200[3] |
| α4β2 | >10,000[2] | >30,000[3] |
| α4β4 | >10,000[2] | >30,000[3] |
| α6/α3β2β3 | >10,000[2] | 144[1] |
| α6/α3β4 | >10,000[1] | 982[1] |
| α7 | 4,660[2] | >30,000[3] |

*Values shown are in nM;
[1] value from Vincler et al. (2006);
[2] values from Ellison et al. (2006);
[3] values from Clark et al. (2006).
ND, not determined.

Example 2

Chronic Constriction Injury Studies

Methods

Animals:

Male Sprague-Dawley rats (200-300 g; Harlan) were used for these studies. All animals were housed in pairs and had free access to food and water. All experiments were performed in accordance with the regulations of Wake Forest University School of Medicine Animal Care and Use Committee.

Chronic Constriction Injury:

Rats underwent loose ligation of the sciatic nerve as described previously by Bennett and Xie (1988) but with slight modification. Briefly, rats were anesthetized with halothane (2-3% halothane in 100% oxygen), the left sciatic nerve was exposed at mid-thigh level and two 4-0 chromic gut sutures were loosely ligated around the sciatic nerve approximately 1 mm apart. The incision was closed with 4-0 silk suture.

Behavioral Testing:

All behavioral tests were conducted between the hours of 9:00 AM and 4:00 PM. No differences in baseline paw withdrawal thresholds (PWT) were noted during these hours. Paw withdrawal thresholds were determined for left and right hind paws using the Randall-Selitto paw pressure technique (Randall and Selitto 1957). The Analgesy-meter (Ugo Basile, Italy) uses a Teflon plinth to apply a constant rate of increasing pressure (16 g per second) to the hind paws. The cut-off pressure was 250 g. For the Randall-Selitto test, animals were first subjected to 4 training sessions to stabilize baseline responses (Taiwo et al. 1989). Hind paws were alternately tested 3 times with a 5 minute inter-trial interval.

Seven days following chronic constriction injury (CCI) of the sciatic nerve, paw withdrawal thresholds (PWT) were measured to confirm the development of mechanical hypersensitivity. Mechanical hypersensitivity was defined as the presence of at least a 20% decrease in PWT compared to pre-CCI baselines. Rats not exhibiting mechanical hypersensitivity were discarded. Rats exhibiting mechanical hypersensitivity were injected with RgIA (0.02 or 0.2 nmol in 200 µl physiological saline) intramuscularly and PWTs were measured hourly for 5 hours and at 24 hours post-RgIA administration. This regimen was repeated daily for 5-7 days.

Immunohistochemistry:

Following behavioral testing on Day 5 or 7 post-RgIA administration, rats were deeply anesthetized with pentobarbital and perfused transcardially with 0.01M PBS+1% sodium nitrite followed by 4% paraformaldehyde (400 mL). The left (injured) and right (uninjured) sciatic nerves were removed and post-fixed in 4% paraformaldehyde (2-3 hours) followed by 30% sucrose (48-72 hours). Tissue was embedded in Tissue-Tek O.C.T. Compound (Sakura Finetek, USA) and cut transversely at 16 µm on a Leica CM3000 cryostat.

Immunohistochemistry was performed using standard biotin-streptavidin techniques. For all immunohistochemistry, sciatic nerve sections were washed in 0.01M phosphate-buffered saline+0.15% Triton-X 100 (PBS+T) and incubated in 0.3% $H_2O_2$ (15 min). Following further washes in PBS+T, sections were incubated in 50% alcohol (45 min), washed in PBS+T, and blocked with 1.5% normal goat serum for 1 hour. Sections were incubated with primary antibodies to CD2 (1:1000, Serotec), CD68 (ED1) (1:1000, Serotec), or ChAT (1:1000, Chemicon) primary antibodies overnight at 4° C. Sections were washed in PBS+T, incubated in biotinylated goat anti-rabbit (ChAT) or anti-mouse (CD2, ED1) antibody (Vector Laboratories) for 1 hour at room temperature, washed in PBS+T and incubated for 1 hour in streptavidin linked horseradish peroxidase (ABC Elite Kit, Vector Laboratories). Antibodies were visualized using the enhanced glucose-nickel-diaminobenzidine method. Images were captured on a Leica Axioplan2 light microscope at 10× magnification. Positively labeled objects were identified for counting using SigmaScan Pro 5 at a preset intensity threshold. For sciatic nerve slices, 4 non-consecutive slices were quantified for ChAT, CD2, and ED1 staining.

Statistical Analysis:

Behavioral data are presented as the mean±the standard error and were analyzed using one-way ANOVA. Immunohistochemical data were analyzed using Student's T test.

Results

Figure 2:
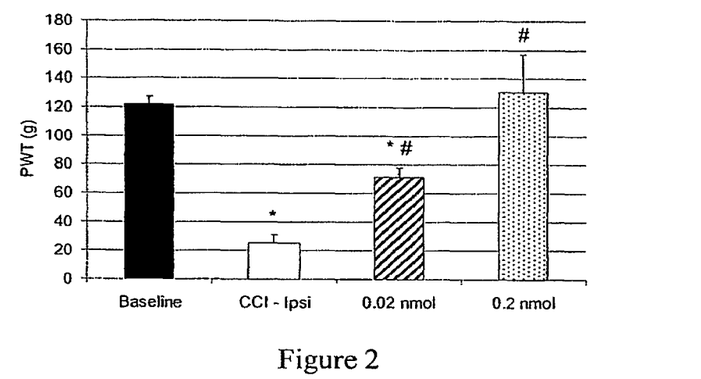
FIG. 2 shows that the α9α10 selective peptide, RgIA, increased paw withdrawal threshold (PWT) ipsilateral to chronic constriction injury. Data shown are the mean PWT±S.E.M. *p<0.05 compared to Baseline; # p<0.05 compared to CCI-Ipsi. n=4/group.

RgIA is Antinociceptive:

Chronic constriction injury produced mechanical hypersensitivity within 7 days of sciatic nerve ligation. Paw withdrawal thresholds were reduced from 122±5 g to 26±5 g 7 days post-CCI. The intramuscular administration of RgIA significantly increased PWTs ipsilateral to CCI within 3-4 hours (FIG. 2). Interestingly, the highest dose of RgIA administered completely reversed CCI-induced mechanical hypersensitivity.

Figure 3:
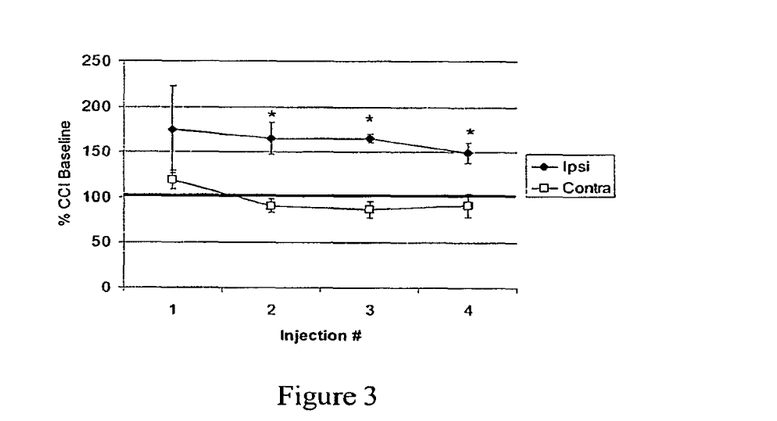
FIG. 3 shows that repeated administration of RgIA significantly decreases CCI-induced mechanical hypersensitivity. The graph depicts the mean percent change±S.E.M. of paw withdrawal thresholds of the ipsilateral (Ipsi) and contralateral (Contra) hind paws of CCI rats 24 hours following once daily injections of 0.2 mmol RgIA. *p<0.05 compared to post-CCI paw withdrawal thresholds; n=4.

In addition to the acute antinociceptive effects of RgIA, repeated once daily intramuscular injections of 0.2 mmol RgIA significantly increased post-CCI baseline PWTs (FIG. 3). Paw withdrawal thresholds in CCI rats ipsilateral to sciatic nerve ligation were increased 65±17% 24 hours after the second administration of RgIA. Paw withdrawal thresholds of the contralateral paw were not significantly altered in CCI rats.

Figure 4:
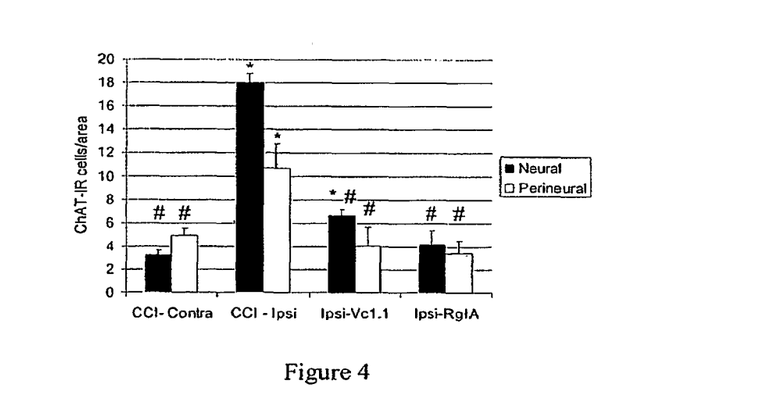
FIG. 4 shows that the mean numbers of ChAT-immunoreactive (ChAT-IR) cells±S.E.M. are shown both ipsilateral (CCI-Ipsi) and contralateral (CCI-Contra) to sciatic nerve ligation. CCI rats treated with Vc1.1 (0.2 nmol) or RgIA (0.2 nmol) for 5-7 days showed reduced numbers of ChAT-IR cells ipsilateral to CCI. *p<0.05 compared to CCI-Contra; # p<0.05 compared to CCI-Ipsi.

RgIA Alters the Peripheral Immune Response to Nerve Injury:

The behavioral effects of RgIA support a role for endogenous acetylcholine (ACh) in nerve injury-induced pain. Therefore, we examined the number of cholinergic-producing cells recruited to the site of nerve injury in CCI rats. As shown in FIG. 4, CCI greatly increased the number of choline acetyltransferase (ChAT) immunoreactive cells in the ligated sciatic nerve and in the immediate vicinity (perineural). Once daily administration of RgIA for 5 days greatly reduced the number of CHAT immunoreactive cells present within the ipsilateral sciatic nerve and in the perineural area. Interestingly, the intramuscular administration of nicotinic antagonist Vc1.1 for 7 days also reduced the number of ChAT positive cells to a similar degree as the α9α10-selective RgIA.

Figure 5:
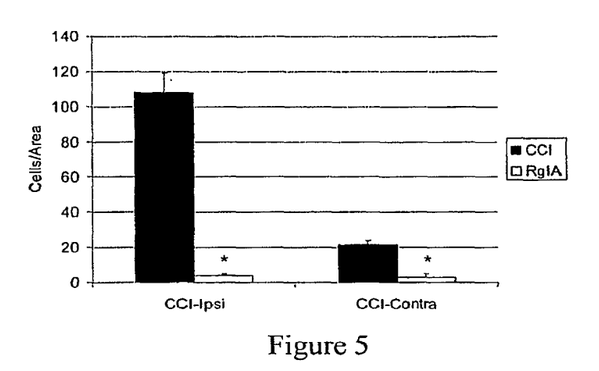
FIG. 5 shows that macrophages are reduced in CCI rats following 5 days of RgIA treatment. The mean number of cells/area±S.E.M. is shown in CCI rats ipsilateral (CCI-Ipsi) and contralateral (CCI-Contra) to nerve ligation. *p<0.05 compared to CCI rats without treatment.

As reported previously, CCI increases the number of ED-1 immunoreactive macrophages and CD2-expressing T cells (FIG. 5). Once daily administration of RgIA (0.2 nmol) for 5 days significantly reduced the number of ED1-immunoreactive macrophages in CCI rats both ipsilaterally and contralaterally.

Example 3

Testing Analogs

Analogs of RgIA, Vc1.1, PeIA and ArIB [V11L; V16A] were prepared using standard techniques well known in the art. These analogs were tested for activity on the α9α10 nAChR subtype as described above in Example 1. The analogs that were prepared and tested and the test results are shown in Table 2.

TABLE 2

Activity of Analogs

| Native Residue | Substituted Residue | $IC_{50}$ |
|---|---|---|
| RgIA | | |
| Arg9 | no substitution | 3.2 nM |
| Arg9 | citrulline9 | 2.4 nM |
| Arg9 | ω-nitro-Arg9 | 2.3 nM |
| Arg9 | homo-Arg9 | >1 µM |
| Arg9 | ornithine9 | >1 µM |
| Arg9 | δ-N-acetyl-ornithine9 | >1 µM |
| Arg9 | Lys9 | >1 µM |
| Tyr10 | iodo-Tyr10 | 3.5 nM |
| Tyr10 | Trp10 | 11 nM |
| Tyr10 | Phe10 | 8.0 nM |
| Arg9, Tyr10 | citrulline9, iodo-Tyr10 | 1.1 nM |
| Arg9, Tyr10 | ω-nitro-Arg9, iodo-Tyr10 | 1.3 nM |
| Ser4 | Ala4 | 14.5 nM |
| Cys12Arg13 | Cys12-amide | 7.8 nM |
| Asp5 | Glu5 | 6.6 µM |
| Pro6 | Val6 | 4.1 µM |
| Arg9 | Ala9 | 13 µM |
| Asp5; Arg7 | His5; Ala7 | >10 µM |
| Arg9 | D-Arg | >3 µM |
| PeIA | | |
| Glu14 | no substitute | 20 nM |
| Glu14 | Asn | ~10 µM |
| ArIB [V11L; V16A] | | |
| His15 | no substitute | >10 µM |
| His 15 | iodo-His15 | 100 nM |

Figure 6:
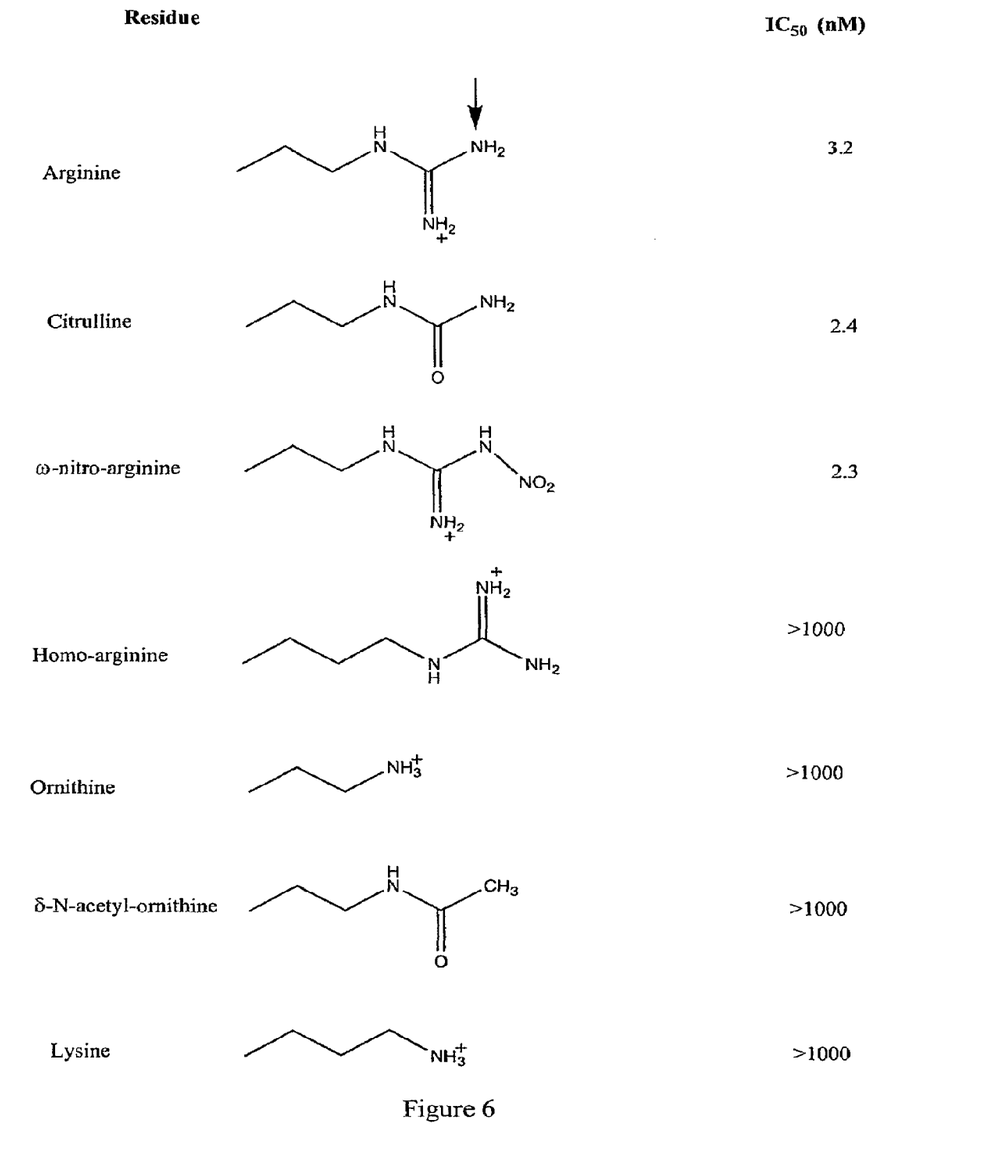
FIG. 6 shows the affect of several substitutions for $Arg_9$ in RgIA. Several of the analogs have improved activity.

The data presented in Table 2 suggests that $Arg_9$ in RgIA is essential for activity. The data further suggests that the nitrogen indicated by the arrow in FIG. 6 is likely essential for activity (perhaps through hydrogen bonding). This was determined by substituting various non-standard amino acids for Arg$_9$. Finally, it is worth noting that the iodo-Tyr10, Arg9 Citrulline IC$_{50}$ is 1.1 nM and that the IC$_{50}$ for iodo-Tyr10, Arg9 omega-nitro-Arg is 1.3 nM. These analogs are more potent than the parent peptide. Although the differences are relatively small, a few fold difference can be very important from a cost of production standpoint. The data in Table 2 further shows that iodo-His at position 15 in ArIB [V11L; V16A] results in a greater than 100 fold shift in activity and that substitution of iodo-His at position 14 of Vc1.1 and PeIA could substantially increase the activity of these peptides.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Arias, H. R. and Blanton, M. P. (2000). Alpha-conotoxins. *Int J Biochem Cell Biol* 32:1017-28.

Armishaw, C. J. and Alewood, P. F. (2005). Conotoxins as research tools and drug leads. *Curr Protein Pept Sci* 6:221-240.

Arredondo, J. et al. (2002). Central role of alpha7 nicotinic receptor in differentiation of the stratified squamous epithelium. *J Cell Biol* 159:325-336.

Azam, L. et al. Alpha-conotoxin BuIA, a novel peptide from *Conus bullatus*, distinguishes among neuronal nicotinic acetylcholine receptors. *J Biol Chem* 280:80-87 (2005).

Bennett, G. J. and Xie, Y. K. (1988). A peripheral mononeuropathy in rat that produces disorders of pain sensation like those seen in man *Pain* 33:87-107.

Clark, R. J. et al. (2006). Fischer, H., Nevin, S. T., Adams, D. J. & Craik, D. J. The synthesis, structural chracterisation and receptor specificity of the alpha-conotoxin Vc1.1. *J Biol Chem Manuscript M604550200*, epub Jun. 5, 2006.

Dutton, J. L. and Craik, D. J. (2001). α-Conotoxins: nicotinic acetylcholine receptor antagonists as pharmacological tools and potential drug leads. *Curr Med Chem* 8:327-344.

Elgoyhen, A. B. et al. (1994). α9: an acetylcholine receptor with novel pharmacological properties expressed in rat cochlear hair cells. *Cell* 79:705-715.

Elgoyhen, A. B. et al. (2001). α10: a determinant of nicotinic cholinergic receptor function in mammalian vestibular and cochlear mechanosensory hair cells. *Proc Natl Acad Sci USA* 98:3501-3506.

Ellison, M. et al. (2006). Alpha-RgIA: a novel conotoxin that specifically and potently blocks the alpha9alpha10 nAChR. *Biochemistry* 45:1511-1517.

Ettinger, L. J. et al. (1978). *Cancer* 41:1270-1273.

Gerzanich, V. et al., (1994). Homomers of α8 and α7 subunits of nicotinic acetylcholine receptors exhibit similar channel but contrasting binding site properties. *Mol. Pharmacol.* 45:212-220.

Gotti, C. and Clementi, F. (2004). Neuronal nicotinic receptors: from structure to pathology. *Prog Neurobiol* 74:363-396.

Haberberger, R. V. et al. (2004). Nicotinic acetylcholine receptor subtypes in nociceptive dorsal root ganglion neurons of the adult rat. *Auton Neurosci* 113:32-42.

Janes, R. W. (2005). alpha-Conotoxins as selective probes for nicotinic acetylcholine receptor subclasses. *Curr Opin Pharmacol* 5:280-292.

Karlin, A. (2002). Emerging structure of the nicotinic acetylcholine receptors. *Nat Rev Neurosci* 3:102-114.

Kurzen, H. et al. (2004). Phenotypical and molecular profiling of the extraneuronal cholinergic system of the skin. *J Invest Dermatol* 123:937-949.

Lang, P. M. et al. (2005). Burgstahler, R., Haberberger, R. V., Sippel, W. & Grafe, P. A *conus* peptide blocks nicotinic receptors of unmyelinated axons in human nerves. *Neuroreport* 16:479-483.

Le Novere, N. et al. (2002). The diversity of subunit composition in nAChRs: evolutionary origins, physiologic and pharmacologic consequences. *J Neurobiol* 53:447-456.

Luer, M. S and Hatton, J. (1993). *Annals Pharmcotherapy* 27:912-921.

Lewis, R. J. (2004). Conotoxins as selective inhibitors of neuronal ion channels, receptors and transporters. *IUBMB Life* 56:89-93.

Lips, K. S. et al. (2002). Coexpression of α9 and α10 nicotinic acetylcholine receptors in rat dorsal root ganglion neurons. *Neuroscience* 115:1-5.

Livett, B. G. et al. (2004). Drugs from the sea: conopeptides as potential therapeutics. *Curr Med Chem* 11:1715-1723.

McIntosh, J. M. et al. (1999). *Conus* peptides targeted to specific nicotinic acetylcholine receptor subtypes. *Annu Rev Biochem* 68:59-88.

McIntosh, J. M. et al. (2005). A novel α-conotoxin, PeIA, cloned from *Conus pergrandis*, discriminates between rat α9α10 and α7 nicotinic cholinergic receptors. *J Biol Chem* 280:30107-30112.

The Merck Manual of Diagnosis and Therapy, 17th Ed. (Merck & Co., Rahway, N.J., 1999).

Nguyen, V. T. et al. (2000). Novel human alpha9 acetylcholine receptor regulating keratinocyte adhesion is targeted by Pemphigus vulgaris autoimmunity. *Am J Pathol* 157: 1377-1391.

Peng, H. et al. (2004). Characterization of the human nicotinic acetylcholine receptor subunit alpha (alpha) 9 (CHRNA9) and alpha (alpha) 10 (CHRNA10) in lymphocytes. *Life Sci* 76:263-280.

Randall, L. O. and Selitto, J. J. (1957). *Arch Int Pharmacodyn* 111:409-418.

*Remington: The Science and Practice of Pharmacy,* 21st Ed., Lippincott Williams & Wilkins, Philadelphia, 2005.

Sandall, D. W. et al. (2003). A novel alpha-conotoxin identified by gene sequencing is active in suppressing the vascular response to selective stimulation of sensory nerves in vivo. *Biochemistry* 42:6904-6911.

Satkunanathan, N. et al. (2005). Alpha-conotoxin Vc1.1 alleviates neuropathic pain and accelerates functional recovery of injured neurones. *Brain Res* 1059:149-158.

Sgard, F. et al. (2002). A Novel Human Nicotinic Receptor Subunit, α10, That Confers Functionality to the α9-Subunit. *Mol Pharmacol* 61:150-159.

Taiwo, Y. O. et al. (1989). The contribution of training to sensitivity in the nociceptive paw-withdrawal test. *Brain Res* 487:148-151.

Terlau, H. and Olivera, B. M. (2004). *Conus* venoms: a rich source of novel ion channel-targeted peptides. *Physiol Rev* 84:41-68.

Vincler, M. et al. (2006). Molecular mechanism for analgesia involving specific antagonism of alpha9alpha10 nicotinic acetylcholine receptors. *Proc Natl Acad Sci USA*

Wang, C. Z., and Chi, C. W. (2004). *Conus* peptides a rich pharmaceutical treasure. *Acta Biochim Biophys Sin* 36:713-723.

Zimm, S. et al. (1984). *Cancer Res* 44:1698-1701.

---

What is claimed is:

1. A method for treating or preventing conditions or disorders associated with the α9α10 subtype of the nicotinic acetylcholine receptor (nAChR) in an individual which comprises administering to an individual in need thereof a therapeutically effective amount of an active agent or a pharmaceutically acceptable salt thereof, wherein the active agent blocks the α9α10 subtype of the nAChR, wherein the active agent is selected from the group consisting of:
α-conotoxin PeIA (SEQ ID NO:3),
  an analog of α-conotoxin Vc1.1 (SEQ ID NO:2), the analog of Vc1.1 being at least one selected from the group consisting of Glu14iodo-His Vc1.1; Glu14iodo-Tyr Vc1.1; Glu14iodo-Trp Vc1.1; Glu14iodo-Phe Vc1.1; an addition to the C-terminus of the preceding analogs; an addition to the N-terminus of the preceding analogs; additions to the C-terminus and N-terminus of the preceding analogs; and replacement of Gly1 in Vc1.1; and
  an analog of α-conotoxin PeIA (SEQ ID NO:3), the analog of PeIA being at least one selected from the group consisting of Glu14iodo-His PeIA; Glu14iodo-Tyr PeIA; Glu14iodo-Trp PeIA; Glu14iodo-Phe PeIA; an addition to the C-terminus of PeIA or the preceding analogs; an addition to the N-terminus of PeIA or the preceding analogs; additions to the C-terminus and N-terminus of PeIA or the preceding analogs; and replacement of Gly1 in PeIA.

2. The method of claim 1, wherein the condition is pain and the administration of the active agent alleviates pain in the individual.

3. The method of claim 1, wherein the condition is inflammation mediated by immune cells and the administration of the active agent reduces inflammation.

4. The method of claim 3, wherein the inflammation is associated with rheumatic diseases.

5. A method of inhibiting migration of immune cells in an individual in need thereof which comprises administering to an individual an immune cell migration-inhibiting amount of an active agent or a pharmaceutically acceptable salt thereof, wherein said active agent blocks the α9α10 subtype of the nicotinic acetylcholine receptor (nAChR), wherein the active agent is selected from the group consisting of:
α-conotoxin PeIA (SEQ ID NO:3),
  an analog of α-conotoxin Vc1.1 (SEQ ID NO:2), the analog of Vc1.1 being at least one selected from the group consisting of Glu14iodo-His Vc1.1; Glu14iodo-Tyr Vc1.1; Glu14iodo-Trp Vc1.1; Glu14iodo-Phe Vc1.1; an addition to the C-terminus of the preceding analogs; an addition to the N-terminus of the preceding analogs; additions to the C-terminus and N-terminus of the preceding analogs; and replacement of Gly1 in Vc1.1; and
  an analog of α-conotoxin PeIA (SEQ ID NO:3), the analog of PeIA being at least one selected from the group consisting of Glu14iodo-His PeIA; Glu14iodo-Tyr PeIA; Glu14iodo-Trp PeIA; Glu14iodo-Phe PeIA; an addition to the C-terminus of PeIA or the preceding analogs; an addition to the N-terminus of PeIA or the preceding analogs; additions to the C-terminus and N-terminus of PeIA or the preceding analogs; and replacement of Gly1 in PeIA.

6. A method for identifying drug candidates for use as treating or preventing conditions or disorders associated with the α9α10 subtype of the nicotinic acetylcholine receptor (nAChR) or for inhibiting the migration of immune cells comprising:
screening a drug candidate agent for its ability to block the activity of the α9α10 subtype of the nAChR, wherein screening the drug candidate agent comprises displacing a labeled α-conotoxin from the α9α10 subtype of the nAChR by a candidate drug agent and measuring the labeled α-conotoxin, wherein a decrease in labeled α-conotoxin indicates displacement of the labeled α-conotoxin from the α9α10 subtype of the nAChR, and identifies the candidate drug agent as a drug candidate,
wherein the α-conotoxin is selected from the group consisting of:
  an analog of α-conotoxin RgIA (SEQ ID NO:1), the analog of RgIA being at least one selected from the group consisting of Arg9citrulline RgIA; Arg9ω-nitro-Arg RgIA; Tyr10iodo-Tyr RgIA; Tyr10Trp RgIA; Tyr10Phe RgIA; Arg9citrulline, Tyr10iodo-Tyr RgIA; Arg9ω-nitro-Arg, Tyr10iodo-Tyr RgIA; Ser4Ala RgIA; RgIA-Cys-amide; an addition to the C-terminus of RgIA or the preceding analogs; an addition to the N-terminus of the preceding analogs; additions to the C-terminus and N-terminus of RgIA or the preceding analogs; replacement of Arg13 in RgIA, and replacement of Gly1 in RgIA;
  an analog of α-conotoxin Vc1.1 (SEQ ID NO:2), the analog of Vc1.1 being at least one selected from the group consisting of Glu14iodo-His Vc1.1; Glu14iodo-Tyr Vc1.1; Glu14iodo-Trp Vc1.1; Glu14iodo-Phe Vc1.1; an addition to the C-terminus of Vc1.1 or the preceding analogs; an addition to the N-terminus of Vc1.1 or the preceding analogs; additions to the C-terminus and N-terminus of Vc1.1 or the preceding analogs; and replacement of Gly1 in Vc1.1; and
  an analog of α-conotoxin PeIA (SEQ ID NO:3), the analog of PeIA being at least one selected from the group consisting of Glu14iodo-His PeIA; Glu14iodo-Tyr PeIA; Glu14iodo-Trp PeIA; Glu14iodo-Phe PeIA; an addition to the C-terminus of PeIA or the preceding analogs; an addition to the N-terminus of PeIA or the preceding analogs; additions to the C-terminus and N-terminus of PeIA or the preceding analogs; and replacement of Gly1 in PeIA.

7. A method for identifying drug candidates for use in treating or preventing conditions or disorder associated with the α9α10 subtype of the nicotinic acetylcholine receptor (nAChR) or for inhibiting the migration of immune cells, the method comprising carrying out an in vitro or in vivo biological assay on a drug candidate and carrying out the same assay on an α-conotoxin, wherein the results obtained from the biological assay on the drug candidate and the α-conotoxin are compared, wherein the α-conotoxin is selected from the group consisting of:
  an analog of α-conotoxin RgIA (SEQ ID NO:1), the analog of RgIA being at least one selected from the group consisting of Arg9citrulline RgIA; Arg9ω-nitro-Arg RgIA; Tyr10iodo-Tyr RgIA; Tyr10Trp RgIA; Tyr10Phe RgIA; Arg9citrulline, Tyr10iodo-Tyr RgIA; Arg9ω-nitro-Arg, Tyr10iodo-Tyr RgIA; Ser4Ala RgIA, RgIA-Cys-amide; an addition to the C-terminus of RgIA or the preceding analogs; an addition to the N-terminus of the preceding analogs; additions to the C-terminus and N-terminus of RgIA or the preceding analogs; replacement of Arg13 in RgIA and replacement of Gly1 in RgIA;
  an analog of α-conotoxin Vc1.1 (SEQ ID NO:2), the analog of Vc1.1 being at least one selected from the group consisting of Glu14iodo-His Vc1.1; Glu14iodo- Tyr Vc1.1; Glu14iodo-Trp Vc1.1; Glu14iodo-Phe Vc1.1; an addition to the C-terminus of Vc1.1 or the preceding analogs; addition to the N-terminus of Vc1.1 or the preceding analogs; additions to the C-terminus and N-terminus of Vc1.1 or the preceding analogs; and replacement of Gly1 in Vc1.1; and an analog of α-conotoxin PeIA (SEQ ID NO:3), the analog of PeIA being at least one selected from the group consisting of Glu14iodo-His PeIA; Glu14iodo-Tyr PeIA; Glu14iodo-Trp PeIA; Glu14iodo Phe PeIA; an addition to the C-terminus of PeIA or the preceding analogs; an addition to the N-terminus of PeIA or the preceding analogs; additions to the C-terminus and N-terminus of PeIA or the preceding analogs; and replacement of Gly1 in PeIA.

8. A method for treating or preventing conditions or disorders associated with the α9α10 subtype of the nicotinic acetylcholine receptor (nAChR) in an individual which comprises administering to an individual in need thereof a therapeutically effective amount of an active agent or a pharmaceutically acceptable salt thereof, wherein the active agent blocks the α9α10 subtype of the nAChR, wherein the active agent is selected from the group consisting of:

an analog of α-conotoxin RgIA (SEQ ID NO:1), the analog of RgIA being at least one selected from the group consisting of Arg9citrulline RgIA; Arg9ω-nitro-Arg RgIA; Tyr10iodo-Tyr RgIA; Tyr10Trp RgIA; Tyr10Phe RgIA; Arg9citrulline, Tyr10iodo-Tyr RgIA; Arg9ω-nitro-Arg, Tyr10iodo-Tyr RgIA; Ser4Ala RgIA; RgIA-Cys-amide; an addition to the C-terminus of RgIA or the preceding analogs; an addition to the N-terminus of the preceding analogs; additions to the C-terminus and N-terminus of RgIA or the preceding analogs; replacement of Arg13 in RgIA, and replacement of Gly1 in RgIA.

9. The method of claim 8, wherein the condition is pain and the administration of the active agent alleviates pain in the individual.

10. The method of claim 8, wherein the condition is inflammation mediated by immune cells and the administration of the active agent reduces inflammation.

11. The method of claim 10, wherein the inflammation is associated with rheumatic diseases.

12. A method of inhibiting migration of immune cells in an individual in need thereof which comprises administering to an individual an immune cell migration-inhibiting amount of an active agent or a pharmaceutically acceptable salt thereof, wherein said active agent blocks the α9α10 subtype of the nicotinic acetylcholine receptor (nAChR), wherein the active agent is selected from the group consisting of:

an analog of α-conotoxin RgIA (SEQ ID NO:1), the analog of RgIA being at least one selected from the group consisting of Arg9citrulline RgIA; Arg9ω-nitro-Arg RgIA; Tyr10iodo-Tyr RgIA; Tyr10Trp RgIA; Tyr10Phe RgIA; Arg9citrulline, Tyr10iodo-Tyr RgIA; Arg9ω-nitro-Arg, Tyr10iodo-Tyr RgIA; Ser4Ala RgIA; RgIA-Cys-amide; an addition to the C-terminus of RgIA or the preceding analogs; an addition to the N-terminus of RgIA or the preceding analogs; additions to the C-terminus and N-terminus of RgIA or the preceding analogs; replacement of Arg13 in RgIA, and replacement of Gly1 in RgIA.

* * * * *

UNITED STATES PATENT AND TRADEMARK OFFICE
CERTIFICATE OF CORRECTION

PATENT NO. : 9,717,775 B2  
APPLICATION NO. : 12/307953  
DATED : August 1, 2017  
INVENTOR(S) : J. M. McIntosh et al.

Page 1 of 1

It is certified that error appears in the above-identified patent and that said Letters Patent is hereby corrected as shown below:

On the Title Page

| Item (74) | Attorney, | "Christensen O'Connore Johnson Kindness PLLC" should |
| Column 2 | Agent, or | read --Christensen O'Connor Johnson Kindness PLLC-- |
|  | Firm |  |

In the Claims

Column 20     Line 44     "disorder" should read --disorders--  
(Claim 7,     Line 2)

Signed and Sealed this  
Fifth Day of June, 2018

Andrei Iancu  
*Director of the United States Patent and Trademark Office*